US009046404B2

(12) United States Patent
Welle

(10) Patent No.: US 9,046,404 B2
(45) Date of Patent: Jun. 2, 2015

(54) MEASURING APPARATUS, CONTROL APPARATUS AND MEASURING DEVICE FOR FILL-LEVEL MEASURING

(75) Inventor: Roland Welle, Oberwolfach (DE)

(73) Assignee: VEGA GRIESHABER KG, Wolfach (DE)

( * ) Notice: Subject to any disclaimer, the term of this patent is extended or adjusted under 35 U.S.C. 154(b) by 678 days.

(21) Appl. No.: 13/328,062

(22) Filed: Dec. 16, 2011

(65) Prior Publication Data

US 2012/0323503 A1 Dec. 20, 2012

Related U.S. Application Data

(60) Provisional application No. 61/423,798, filed on Dec. 16, 2010.

(30) Foreign Application Priority Data

Dec. 16, 2010 (WO) ............... PCT/EP2010/069992

(51) Int. Cl.
*G01F 23/26* (2006.01)
*G01F 23/284* (2006.01)
(Continued)

(52) U.S. Cl.
CPC .............. *G01F 23/26* (2013.01); *G01F 23/284* (2013.01); *G01F 25/0061* (2013.01); *G01F 23/24* (2013.01); *G01F 23/263* (2013.01); *G01F 23/2962* (2013.01)

(58) Field of Classification Search
CPC . G01F 23/284; G01F 23/296; G01F 23/2962; G01F 1/66; G01F 23/263; G01F 23/268

USPC .......................................................... 702/55
See application file for complete search history.

(56) References Cited

U.S. PATENT DOCUMENTS 5,038,611 A * 8/1991 Weldon et al. .............. 73/290 V
6,701,783 B2 3/2004 Fehrenbach et al.
(Continued)

FOREIGN PATENT DOCUMENTS

DE 101 03 056 8/2001
DE 100 44 888 4/2002
(Continued)

OTHER PUBLICATIONS

Devine, "Radar level measurement—The users guide", VEGA Controls, ISBN 0-9538920-0-X, 2000, 22 sheets, Aug. 15, 2000.
(Continued)

*Primary Examiner* — John Breene
*Assistant Examiner* — Lynda Dinh
(74) *Attorney, Agent, or Firm* — Fay Kaplun & Marcin, LLP

(57) ABSTRACT

A measuring apparatus includes a first waveguide device with a first feed in device. The first waveguide device carries out a first measurement. The apparatus further includes a measuring device carrying out a second measurement. The first waveguide device is adapted for dividing a container interior into at least one first spatial region and into a second spatial region. The first waveguide device is further adapted for guiding a first electromagnetic wave in the first spatial region, which the first electromagnetic wave has been coupled into the first waveguide device via the first feed in device. The measuring device is adapted for carrying out the second measurement on the first waveguide device in the second spatial region.

12 Claims, 7 Drawing Sheets

(51) Int. Cl.
*G01F 25/00* (2006.01)
*G01F 23/24* (2006.01)
*G01F 23/296* (2006.01)

(56) References Cited

U.S. PATENT DOCUMENTS

| | | |
|---|---|---|
| 7,334,451 B1 | 2/2008 | Fauveau |
| 7,639,177 B2 * | 12/2009 | Welle et al. .................. 342/124 |
| 7,965,087 B2 | 6/2011 | Reimelt et al. |
| 2001/0010171 A1 | 8/2001 | Atkinson |
| 2004/0182149 A1 * | 9/2004 | Balin et al. ................. 73/290 V |
| 2008/0302439 A1 * | 12/2008 | Spanke et al. ..................... 141/1 |
| 2009/0211808 A1 * | 8/2009 | Falk et al. ..................... 174/667 |
| 2009/0212997 A1 * | 8/2009 | Michalski ..................... 342/137 |
| 2009/0299662 A1 * | 12/2009 | Fehrenbach et al. ............ 702/55 |
| 2010/0313654 A1 | 12/2010 | Malinovskiy et al. |

FOREIGN PATENT DOCUMENTS

| | | |
|---|---|---|
| DE | 10 2006 019 191 | 10/2007 |
| DE | 10 2007 042 043 | 3/2008 |
| DE | 10 2007 061 574 | 6/2009 |
| RU | 2 276 334 | 5/2006 |
| SU | 1 688 120 | 10/1991 |
| WO | 2006/103200 | 10/2006 |
| WO | 2010/040580 | 4/2010 |
| WO | 2010/071564 | 6/2010 |

OTHER PUBLICATIONS

"Users Guide Levelflex FMP55", Endress & Hauser, 48 sheets, Jul. 6, 2010.

* cited by examiner

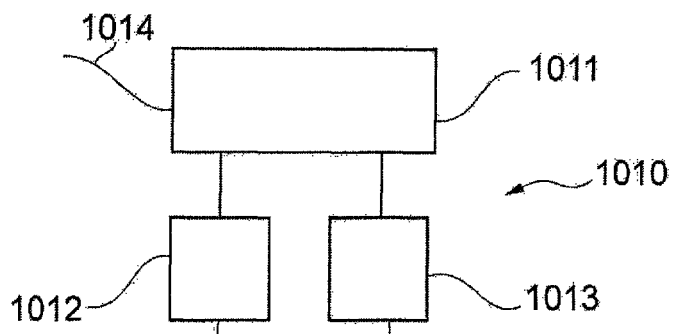
Fig. 10A
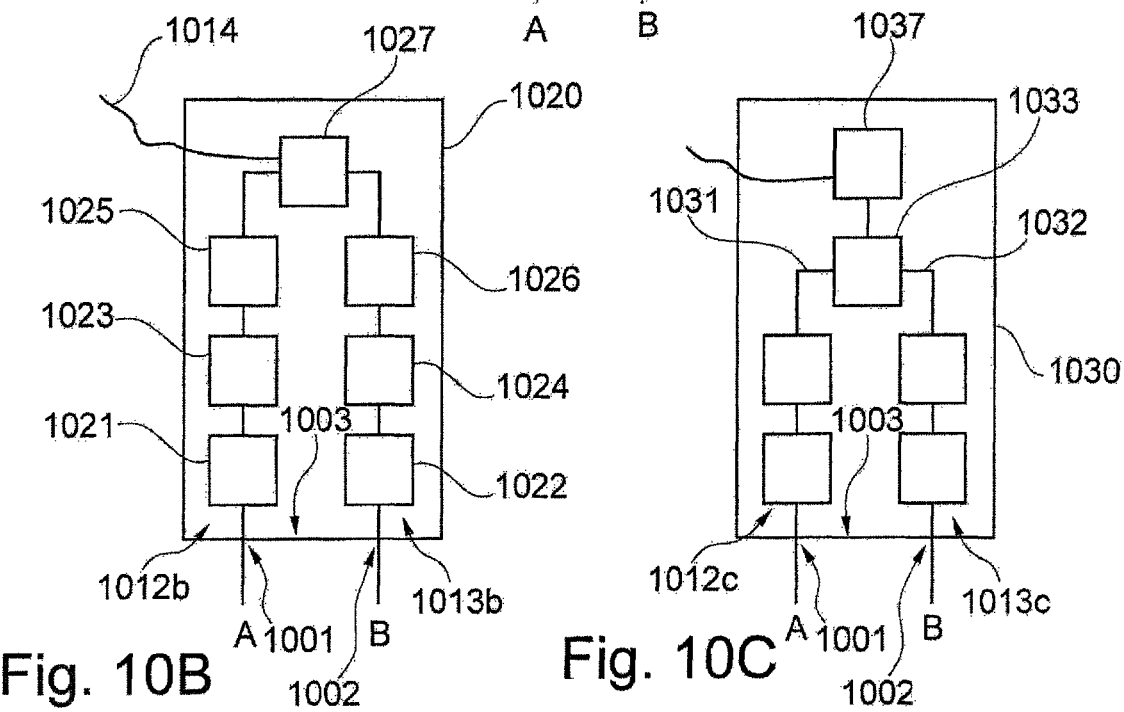
Fig. 10B
Fig. 10C
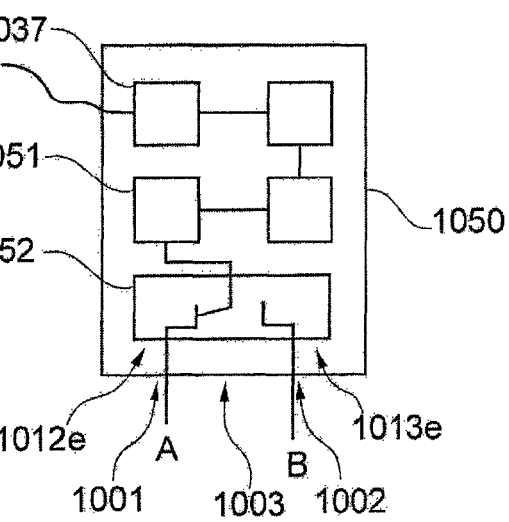
Fig. 10D
Fig. 10E

MEASURING APPARATUS, CONTROL APPARATUS AND MEASURING DEVICE FOR FILL-LEVEL MEASURING

REFERENCE TO RELATED APPLICATIONS

This application claims the benefit of the filing date of PCT Patent Application Serial No. PCT/EP2010/069992 filed 16 Dec. 2010 and U.S. Provisional Patent Application Ser. No. 61/423,798 filed 16 Dec. 2010, the disclosure of both applications is hereby incorporated by reference.

TECHNICAL FIELD

The present invention relates to the field of measuring technology, and in particular the invention relates to a measuring apparatus, a control apparatus, a measuring device, a method for operating the measuring apparatus, a computer-readable storage medium, the use of the measuring apparatus for emulsion measuring and the use of the measuring apparatus for determining media characteristics.

BACKGROUND INFORMATION

In fill-level sensors operating according to the FMCW (frequency modulated continuous wave) method or pulse-transit time method electromagnetic or acoustic waves are emitted in the direction of a feed material surface. Subsequently a sensor records the echo signals reflected by the feed material, the container internals and the container itself, and from them derives the respective fill level.

The book "Radar level measurement—The users guide", ISBN 0-9538920-O-X, by Peter Devine, VEGA Controls, 2000 describes the basic design of radar fill-level sensors.

The printed publication DE 10 2007 061 574 A1 describes a method for fill-level measuring in which method a reflected component of a signal and a capacitance between a capacitive probe and a reference electrode are measured.

There may be a need to make possible the effective measuring in particular of fill levels and limit levels as well as of characteristics of a feed material.

SUMMARY OF THE INVENTION

According to one aspect of the present invention, a measuring apparatus, in particular a measuring apparatus for measuring fill levels and/or limit levels, a control apparatus, a measuring device, a method for operating the measuring apparatus, a computer-readable storage medium, the use of the measuring apparatus for emulsion measuring, and the use of the measuring apparatus for determining media characteristics may be described.

For example, according to one aspect of the present invention a measuring apparatus may be stated that comprises a first waveguide device with a first feed in device, and a measuring device or gauge device. The first waveguide device can be designed for carrying out a first measurement, and the measuring device can be adapted for carrying out a second measurement. The first waveguide device may furthermore be designed for dividing a container interior into at least one first spatial region and into a second spatial region. Moreover, the first waveguide device can be adapted for guiding a first electromagnetic wave in the first spatial region, for example a guided microwave, which may have been coupled into the first waveguide device by way of the first feed in device. By means of the first measurement, in one example a fill level in the first spatial region may be able to be determined. A feed in device or a couple device may be adapted to couple or to feed in an electromagnetic wave into a conductor or wave guide.

The measuring device may be adapted for carrying out the second measurement on the first waveguide device or on at least one part of the first waveguide device. The second measurement can take place in the second spatial region. In particular, the measuring device can be adapted for measuring a fill level.

For measuring the first waveguide device, the second spatial region or a fill level in the second spatial region, the measuring device in one example may also utilize an electromagnetic wave or generally any transit-time measuring method. In another exemplary embodiment the measuring device may utilize an alternative measuring method, for example an acoustic, a conductive, a capacitive or an inductive measuring method. The measuring signal which the measuring method of the measuring device may utilize can be coupled into the measuring device by way of a further coupling device.

The first waveguide device may be adapted for spacing apart the first feed in device of the first waveguide device from the measuring device so that the first electromagnetic wave can propagate in the first spatial region at a predeterminable distance from the second spatial region provided for carrying out the second measurement by means of the measuring device. The first spatial region can differ from the second spatial region. For example, the fill level at different locations may be determinable with different methods of fill-level measuring by means of a shared measuring apparatus. In one example the spatial regions may be disjunct. In another example the two spatial regions may extend so as to be essentially parallel to each other. The spatial regions may be arranged at various locations along a direction that is essentially perpendicular to a longitudinal axis of the first waveguide device or perpendicular to a direction of propagation of the first electromagnetic wave. The first waveguide device may thus be adapted both for spacing apart the spatial regions, and for spacing apart the feed in devices or the waveguide devices and/or the measuring device.

According to another aspect of the present invention, the measuring apparatus may comprise a spacer device, wherein the spacer device is adapted for spacing apart the first feed in device of the first waveguide device from the measuring device. The spacer device may be adapted for spacing apart the first waveguide device from the measuring device so that the first electromagnetic wave can propagate at a distance from the measuring device, which distance is predeterminable by means of the spacer device. In other words the arrangement of the first waveguide device and of the measuring device in the measuring apparatus may permit fill-level measuring inside a container at different locations. The spacer device can additionally or solely ensure separation of the spatial regions so that it may be ensured that the first measurement takes place essentially in the first spatial region, and the second measurement takes place essentially in the second spatial region.

According to another aspect of the present invention, a control apparatus may be stated. The control apparatus may comprise an evaluation device, a first measuring apparatus with a first connection device, and a second measuring device with a second connection device. Furthermore, the control apparatus may comprise a connection spacer device and a collective interface. The first measuring apparatus and the second measuring apparatus may be connected to the evaluation device, and may be designed for providing a first electromagnetic wave by way of the first connection device or for providing a measuring signal for measuring at least part of the first waveguide device by way of the second connection device. The measuring signal can be provided on a measuring device.

The first connection device may be spaced apart from the second connection device by means of the connection spacer device so that the first electromagnetic wave can be provided at a distance from the measuring signal, which distance is predeterminable by means of the connection spacer device. The first measuring device may be adapted for determining and providing a first measured value of a measurement with the first electromagnetic wave in a first spatial region, wherein provision of the first measured value to the evaluation device may take place. The first electromagnetic wave may be provided for the first spatial region.

The second measuring device may be adapted for determining and for providing a second measured value. The second measured value may be the result of a measurement with the measuring signal in a second spatial region, wherein the second measured value may also be provided to the evaluation device. The evaluation device may be adapted, after receiving the first measured value and the second measured value, for converting the first measured value and the second measured value to a shared measured value or to a common measured value and for providing this shared measured value at the collective interface. In other words, in the evaluation device, reprocessing of the first measured value of a first measurement, and of a second measured value of a second measurement may take place, wherein the evaluation may take place according to predeterminable criteria.

It is also possible to provide an echo curve or a reflection signal as the first measured value or as the second measured value. From the reflection signal the echo curve can be generated, and from the echo curve a measured value or a characteristic value relating to the corresponding spatial region can be determined. An echo curve can illustrate the reflection conditions in a spatial region.

For evaluation of the first measured value and/or of the second measured value the underlying measuring method may be determined by the respective measuring device. A measuring device or the control apparatus may detect the type of a connected measuring apparatus.

The type of evaluation, in particular the calculation method, may also be settable by way of a setting device on the control apparatus.

According to another aspect of the invention, a measuring device for fill-level measuring and/or for limit-level measuring or limit-value measuring may be described. The measuring device may comprise the measuring apparatus according to the invention and the control apparatus according to the invention, wherein the measuring apparatus may be linked with or connected electrically and/or mechanically to the control apparatus. Mechanical connection may, for example, be able to be established by way of a screw thread and/or a bayonet connection.

The measuring apparatus and/or the control apparatus may thus be suitable for fill-level measuring or for limit-level measuring.

According to yet another aspect of the present invention, a method may be described that may serve to operate the measuring apparatus according to the invention. The method may comprise the provision of a first electromagnetic wave in a first waveguide device by way of a first connection device. The first electromagnetic wave may be provided in a first spatial region of the first waveguide device. Furthermore, the method may comprise measuring at least part of the first waveguide device with a measuring signal that is provided by way of a second connection device. Measuring the first waveguide device by means of the measuring device may take place in a second spatial region. In one example the first connection device may be spaced apart from the second connection device by means of a connection spacer device.

The first electromagnetic wave and the measuring signal may be provided in a locally separated manner for a measurement.

Essentially after carrying out the measurements, a first measured value of a measurement with the first electromagnetic wave may be provided to an evaluation device, and a second measured value of a measurement with the measuring signal may also be provided to the evaluation device. The first measured value and/or the second measured value may also be an echo curve in an analog or digital form, which echo curve has been determined. The provided first and second measured values may be converted or taken together in the evaluation device so as to form a shared measured value, and this shared measured value may be provided to a collective interface of the evaluation device. The collective interface may in one example be an external interface. In one example the evaluation device can also form part of an output unit.

According to yet another exemplary embodiment a computer-readable storage medium may be described on which a program code may be stored which when executed by a processor may instruct the processor to carry out the method according to the invention.

According to another aspect a program element may be described which when executed by a processor may instruct the processor to carry out the method according to the invention.

The control apparatus may be implemented as a single integrated circuit (IC).

According to yet another aspect of the present invention, the use of the measuring apparatus and/or the control apparatus for emulsion measuring may be described.

According to yet another aspect of the present invention, the use of the measuring apparatus and/or of the control apparatus for determining media characteristics may be described, in particular of media characteristics of a liquid or of a content of a container.

It may be considered an aspect of the present invention that by means of at least two measurements, which are essentially carried out at a predeterminable distance, measuring results, fill levels or echo curves may be provided which essentially reflect the same circumstances. Because of different evaluation methods of the measuring results obtained with the different measuring methods, parameters may be able to be determined by means of which a statement may be made that differs from a fill level. For example, such a statement may relate to the content or a mixing ratio of a content of a medium in a container. Moreover, a separating layer position may be determined. Furthermore, a characteristic value relating to an overlay medium may be able to be determined which is situated above a feed material surface and/or a separating layer surface. An overlay medium can be a lighter-weight second liquid that is situated above a first liquid; steam, gas or a gas mixture. A characteristic value can relate to permeability, permittivity, pressure, temperature, or to a degree of saturation of the overlay medium.

The at least two measurements may be measurements according to different measuring principles. For example, transit time measuring or reflection measuring may be carried out. In another example, fill-level measuring may be carried out on the basis of ultrasound, laser or an electromagnetic wave. Furthermore, it may be also possible for fill-level measuring by means of conductive, inductive or capacitive measuring to be used. In particular, the fill level can be determined in a pipe by means of a conductive or capacitive measuring method. In an exemplary embodiment of the present invention, propagation of two electromagnetic waves at different physical locations may be utilized for determining the characteristic values of interest. In a further exemplary embodiment of the present invention, double fill-level measuring according to a transit time method may be carried out. In other words, for measuring, at least one transit-time measuring method or reflection measuring method may be combined with any other measuring method. In an exemplary embodiment a transit time method may also be combined with a further transit-time measuring method. The difference in the measuring methods may relate to the location at which the respective method may be carried out. The different locations may be different spatial regions or different channels of a measuring apparatus. The channels may be located inside a shared housing of the measuring apparatus.

According to another aspect of the present invention, the measuring apparatus may comprise a measuring device that may be selected from a group of measuring devices, wherein the group may consist of a conductive measuring device, a capacitive measuring device, an inductive measuring device, and an acoustic measuring device. The group may furthermore comprise a second waveguide device with a second feed in device or a second coupling device, wherein the second waveguide device may be designed for guiding a second electromagnetic wave that may have been fed into the second waveguide device by way of the second feed in device. A feed in device may also be used to couple an electromagnetic wave into a wave guide device.

According to yet another aspect of the present invention, the first waveguide device and/or the second waveguide device may be selected from a group of different waveguide devices. The group of waveguide devices may comprise a coaxial conductor, a hollow conductor, a hollow conductor comprising at least one lateral opening, a guiding device for a microwave, a standpipe, a wire, a metal bar and a cord.

The first waveguide device and the measuring device, in particular the second waveguide device, may be taken together in a shared housing. For example, the first waveguide device, too, may be integrated in the measuring device, or the measuring device may be integrated in the first waveguide device. The respective outer device may serve as a housing for the entire measuring apparatus. In this manner a compact configuration of a probe may be implementable so that the probe can be accommodated in just a single process connection of a container. A process connection may be an opening of a container. This opening can also comprise a flange for installing the measuring apparatus and/or a control apparatus.

The shared housing may make possible simple transport of the measuring apparatus. In one example the measuring apparatus may be a probe. Taking together the components of the probe in a shared housing may also facilitate installation of the probe on a control device. The distances between the channels may essentially not be influenced during transport.

According to another aspect of the present invention, the spacer device may be at least one spacer device selected from the group of spacer devices. The group of spacer devices may consists of a bracket, a flange, a container wall, a wall of a hollow conductor or of a waveguide and an isolator.

The spacer device may hold the first waveguide device and the measuring device essentially at a constant distance. In this way the same measured quantity, for example the level of a liquid in a container, may be able to be determined at different locations. The position of the locations may essentially be known by means of the spacer. With the use of special measures, for example lateral openings in a standpipe, it may be made sure that in the individual channels an essentially identical liquid level may be ensured.

According to yet another exemplary embodiment of the present invention, the first waveguide device and the measuring device, in particular the second waveguide device, may be arranged coaxially.

By means of a coaxial arrangement of the waveguide device and of the measuring device, in particular of the first waveguide device and of the second waveguide device, integration of the first waveguide device in the measuring device and vice-versa may be able to be implemented. For example, the first waveguide device may be a metal bar, and the measuring device may be the outer wall of a hollow conductor. The metal bar may comprise a first longitudinal axis, and the hollow conductor may comprise a second longitudinal axis, wherein with a coaxial arrangement the longitudinal axes of the waveguide devices or of the measuring device are essentially situated on top of each other.

According to a further aspect of the present invention, the first waveguide device and/or the second waveguide device may comprise an end, wherein through this end a reference line extends so as to be essentially perpendicular to a direction of propagation of the electromagnetic wave, wherein the first feed in device and the second feed in device are arranged in the essentially equal space relative to this reference line. The reference line may be an imaginary reference line.

Thus the feed in device may be situated so as to be essentially equidistant from a pipe end or a probe end.

According to yet another exemplary embodiment of the present invention, the first feed in device and/or the second feed in device may be at least one feed in device selected from the group of feed in devices. The group of feed in devices may consist of a strip conductor, a loudspeaker, an optocoupler, a laser, an inductive coupler, a capacitive coupler, a loop coupling, a pin coupling and a hole coupling. A coupler or a coupling may be a feed device.

The fed in device may be suitable for stimulating a measuring signal, in particular an electromagnetic wave, an acoustic wave or an optical wave inside the first feed in device and/or the measuring device so that the corresponding signal can propagate in the measuring device or waveguide device.

According to yet another aspect of the present invention, the first feed in device and/or the second feed in device may comprise a connection device, in particular a first connection device and a second connection device, respectively. The connection devices may in each case be at least one connection device that may be selected from the group of connection devices consisting of a high-frequency plug, a high-frequency socket, a high-frequency adapter, a circulator and a directional coupler.

According to yet another aspect of the present invention, the measuring apparatus may be designed as a probe for a fill-level measuring device and/or for a limit-level measuring device.

The probe may, for example, comprise a screw connection or a bayonet connection by means of which connection said probe can be connected to a matching control apparatus or control device in order to form a measuring device or a field device, in particular a field device for fill-level measuring or for limit-level measuring.

According to one aspect a measuring signal may be a current, in particular an electrical current, that can be set depending on a capacitance or inductance.

According to yet another aspect a measuring signal may be a second electromagnetic wave.

Measuring, gauging or ranging the first waveguide device may thus essentially take place not only by means of a capacitive or inductive method, but also by means of a freely propagating or by means of a guided electromagnetic wave. As an alternative it is also possible to use an acoustic wave, for example in the ultrasonic range. The measuring device can thus utilize a further transit-time measuring method or a reflection measuring method.

According to yet another exemplary embodiment of the present invention, the control apparatus may comprise a shared generator for generating the electromagnetic wave and the measuring signal and in particular the first electromagnetic wave and the second electromagnetic wave. Moreover, the control apparatus may comprise a distribution device, wherein the distribution device may be designed for distributing the first electromagnetic wave to the first connection device, and the second electromagnetic wave to the second connection device. In the case of an inductive and/or capacitive measurement the measuring signal can be a current that may be influenced according to a prevailing fill level.

According to another aspect of the present invention, the method for operating the measuring apparatus may comprise the provision of a second electromagnetic wave as a measuring signal. The second electromagnetic wave may be provided by way of the second connection device. It may then be possible to provide to the evaluation device a second measured value of a measurement with the second electromagnetic wave.

It should be noted that different aspects of the invention are described with reference to different objects. In particular, some aspects are described with reference to device-related claims, whereas other aspects are described with reference to method-related claims. However, a person skilled in the art may be able to gather from the description above and the description below that, unless otherwise described, in addition to any combination of characteristics that forms part of a category of objects, any combination of characteristics that relates to different categories of objects may also be considered to be disclosed by this text. In particular, combinations of characteristics of device-related claims with characteristics of method-related claims may have been disclosed.

BRIEF DESCRIPTION OF DRAWINGS

Below, further exemplary embodiments of the present invention are described with reference to figures.

FIG. 10A shows a simple block diagram of a control apparatus according to an exemplary embodiment of the present invention.

FIG. 10B shows a detailed block diagram of a control apparatus with separate signal paths according to an exemplary embodiment of the invention.

FIG. 10C shows a detailed block diagram of a control apparatus with a shared evaluation unit and a shared output unit according to an exemplary embodiment of the present invention.

FIG. 10D shows a detailed block diagram of a control apparatus with an analog switch according to an exemplary embodiment of the present invention.

FIG. 10E shows a detailed block diagram of a control apparatus with a high-frequency change over switch according to an exemplary embodiment of the present invention.

DETAILED DESCRIPTION

Figure 1:
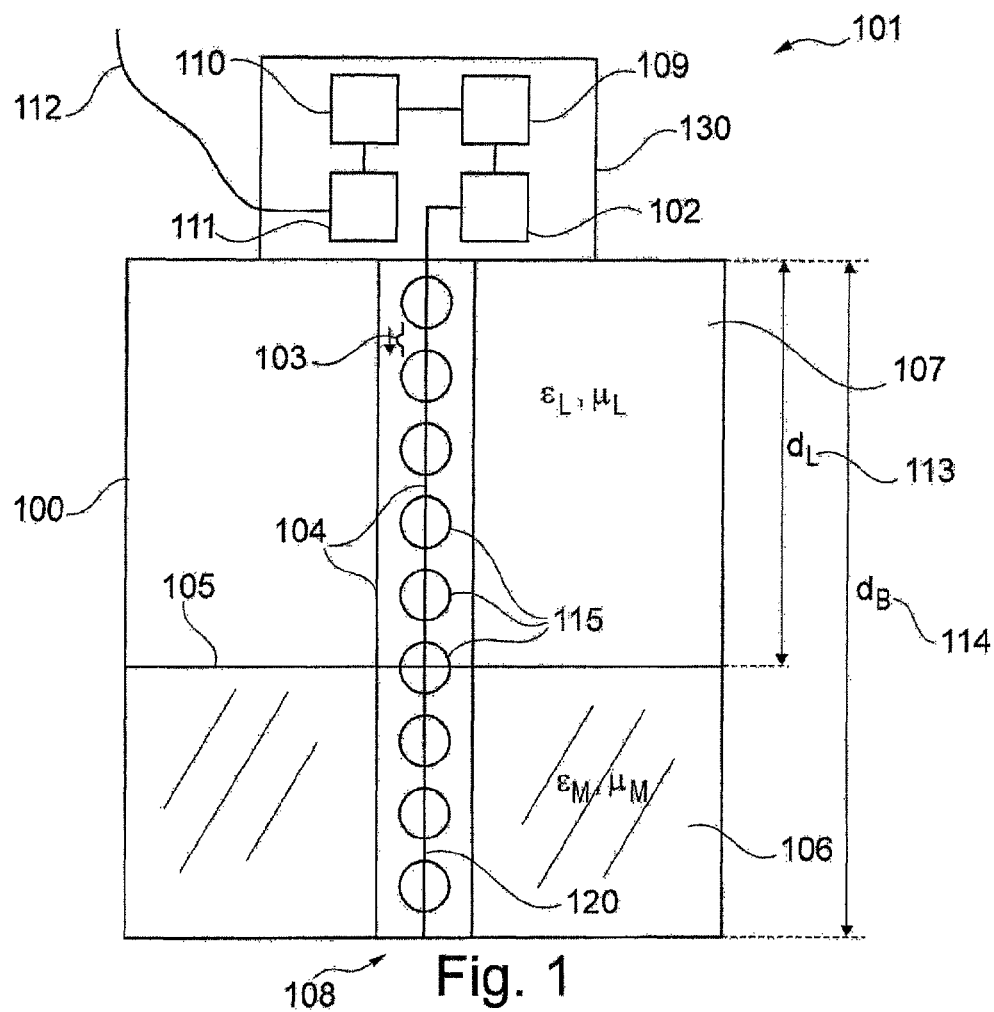
FIG. 1 shows a measuring arrangement for fill-level measuring with a standpipe and a measuring rod according to the method of the guided microwave to provide a better understanding of the present invention.

The illustrations in the figures are diagrammatic and not to scale.

A measuring apparatus can, for example, comprise a first waveguide device and a measuring device, or a first waveguide device and a second waveguide device which are implemented as two devices. The devices can utilize different measuring principles. By means of a standpipe a microwave can be guided; however, it is also possible to measure the capacitance of the standpipe.

When using acoustic or optical waves the signal generated by the fill-level measuring device or by the control apparatus generally-speaking freely propagates in the direction of the feed material surface to be measured. In a unit or a device that utilizes radar waves for measuring the feed material surface, both free propagation in the direction of the medium to be measured, which medium can form the feed material surface, can be considered, and propagation along a guiding device, for example the interior of a hollow conductor, which guiding device guides the radar waves from the fill-level measuring device, in particular from the control apparatus or from the feed in device, to the medium. In devices according to the principle of the guided microwave the high-frequency signals are guided in the interior or along the surface of a waveguide to the medium.

On the surface of the medium to be measured some of the incoming signals are reflected, and after a corresponding transit time return to the fill-level measuring device, in particular to the control apparatus of a fill-level measuring device or of a field device. The non-reflected signal components enter the medium and propagate in it, according to the physical characteristics of the medium, in the direction of the container bottom. These signals are reflected by the container bottom and, after passing through the medium and the overlaid atmosphere or the overlay medium, return to the fill-level measuring device, in particular to a first measuring device or to a second measuring device.

The measuring device receives the signals reflected by various positions and from them determines the distance to the feed material according to a transit-time measuring method.

The determined distance to the feed material is provided towards the outside by way of an external interface. The provision can be implemented in analog form, for example as a 4.20 mA signal on a 4.20 mA interface, or in digital form, for example on a field bus. A field bus can be a HART® bus, a Profibus or a Fieldbus Foundation™ field bus. A further example of an interface may be the I²C (inter-integrated circuit) interface or a computer interface such as RS232, RS485, USB (universal serial bus), Ethernet, FireWire or WLAN (wireless local area network).

Fill-level measuring, separating layer measuring and/or emulsion measuring can take place in various ways. For example, an arrangement for fill-level measuring, separating layer measuring and/or emulsion measuring can comprise at least one measuring apparatus and/or a control apparatus that determines the fill level according to the principle of the guided microwave. In another exemplary embodiment it is, however, also possible to implement an apparatus that in terms of a measuring principle, as a supplement to the guided microwave, or as an alternative to it, utilizes at least one acoustic measuring principle, an optical measuring principle, an inductive measuring principle, a capacitive measuring principle or an essentially freely-radiating measuring principle, in particular with the use of freely-radiating radar waves.

It may be an aspect of the invention to create a device or probe that makes it possible, essentially at the same time, to utilize at least two identical or different measuring principles with only a single device.

FIG. 1 shows an arrangement for fill-level measuring according to the principle of a guided microwave. The arrangement of FIG. 1 utilizes a coaxial standpipe 104 with an inner guide for fill-level measuring. The container 100 is filled with a medium M 106 or a liquid 106 up to a filling height $d_B - d_L$. The filling height is calculated from a difference between two distances, starting with a reference height, for example the location of feeding in the microwave or the location of coupling the microwave. It is assumed that the space above the liquid 107 first is filled with another medium, for example air L. In other words, the space above the liquid 107 first comprises another medium, for example air L The liquid 106 to be measured, and the overlay atmosphere 107 are essentially in the container interior.

A fill-level measuring device 101 operating according to the principle of the guided microwave generates an electromagnetic pulse 103 in a control apparatus 130 by means of a high-frequency unit 102 and couples said electromagnetic pulse 103 into a probe 104, which in the arrangement shown in FIG. 1 is designed as a waveguide 104, after which this pulse propagates in the interior of the waveguide 104 almost at the speed of light in the direction of the feed material surface 105 to be measured. In other words, the fill-level measuring device feeds the pulse 103 into the probe 104.

In the present example the waveguide 104 shown is designed in the form of a coaxial guide. However, any form of a waveguide can be considered as a probe, thus in particular single-wire or multiple-wire lines.

The coaxial guide 104 used for fill-level measuring comprises a pipe that has holes 115, spaced apart from each other so as to be equidistant, in the pipe wall, which holes 115 make it possible for the liquid 106 to be measured to enter the region between the outer guide, e.g. the wall of the pipe 104, and the inner guide 120.

The feed material surface 105 reflects part of the incoming signal energy, whereupon the reflected signal component propagates along the waveguide 104 back to the fill-level measuring device 101 and in particular to the evaluation device of the fill-level measuring device. The non-reflected signal component enters the liquid 106 and propagates in it at greatly reduced speed along the waveguide 104. The speed $c_{Medium}$ of the electromagnetic wave 103 inside the liquid 106 is determined by the material characteristics of the liquid 106:

$$c_{Medium} = \frac{c_0}{\sqrt{\varepsilon_R \cdot \mu_R}}$$

wherein $c_o$ denotes the speed of light in the vacuum, $\varepsilon_R$ denotes the permittivity value of the liquid, and $\mu_R$ denotes the permeability value of the liquid. At the lower end 108 of the waveguide 104 in a bottom region of the container 100 the remaining signal component is also reflected, and after a corresponding transit time returns to the fill-level measuring device 101, in particular to the control apparatus 130. In the fill-level measuring device 101, in particular in the control apparatus 130, the incoming signals are processed by means of the high-frequency unit 102 and are, for example, transformed to a lower-frequency intermediate frequency range (IF range). By means of an analog-digital converter unit 109 (A/D converter) the analog echo curves, which are provided by the high-frequency unit 102, are digitized and made available to an evaluation unit 110. The evaluation unit 110 analyzes the digitized echo curves, and, based on the echos contained therein, according to predeterminable methods determines that echo which has been generated by the reflection from the feed material surface 105. Moreover, the evaluation unit 110 determines the essentially precise distance to this echo. Furthermore, the essentially precise distance to the echo is corrected in such a manner that influences which the overlaid gas atmosphere 107 has on the propagation of the electromagnetic waves are compensated. The compensated distance to the feed material 113, which distance has been calculated in this manner, is provided to an output unit 111 which further processes the particular value according to the specifications of the user, for example by linearization, offset correction, conversion to a filling height $d_B - d_L$. The processed measured value is provided towards the outside on an external communication interface 112. Any interface can be used for such provision, in particular a 4.20 mA current interface, an industrial field bus such as HART®, Profibus, Fieldbus Foundation™ (FF), or also a computer interface such as RS232, RS485, USB (universal serial bus), Ethernet or FireWire.

Figure 2:
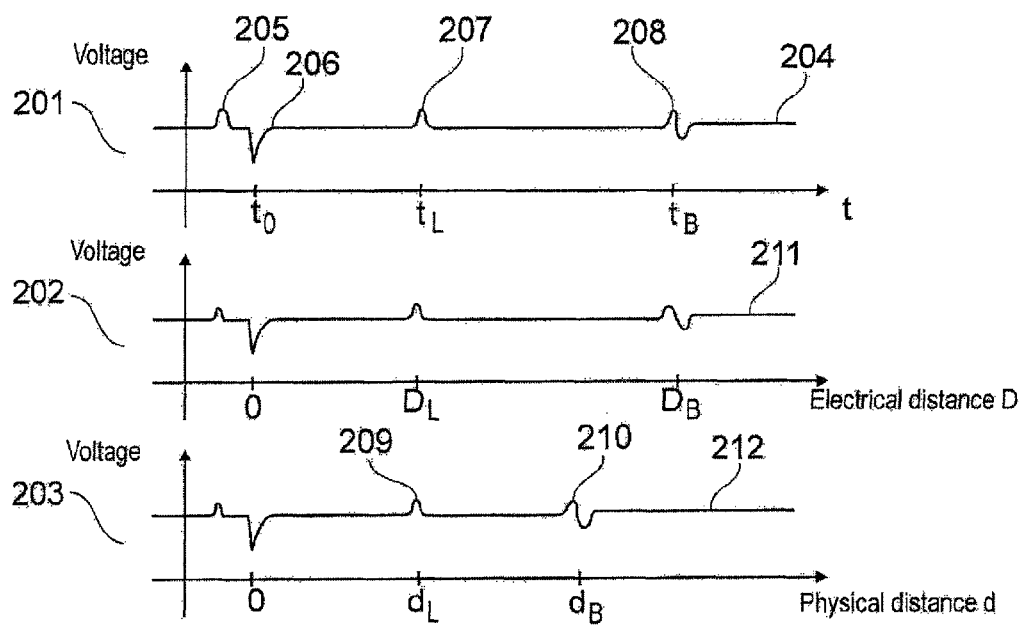
FIG. 2 shows three evaluation curves for echo signal processing to provide a better understanding of the present invention.

FIG. 2 illustrates the steps which in the context of echo signal processing in the evaluation unit 110 are used for compensating the influences of various media. Parts of these steps can be utilized in the evaluation of echo signals.

Curve 201, curve trace 201 or graph 201 first shows the echo curve 204 which has been acquired by the analog-digital converter unit 109 over time and which has been obtained from the reflection signals. The echo curve first comprises the transmission pulse 205. A short time later, at the point in time $t_0$, a first reflection 206 is acquired which has been caused by coupling or feeding in the high-frequency signal into the waveguide 104, e.g. by a feed in device. A further reflection 207 is derived from the feed material surface 105 and is acquired at the point in time $t_L$. Finally, the echo 208 generated by the lower end 108 of the waveguide 104 is acquired at the point in time $t_B$.

In a first processing step the time-dependent curve 204 is transformed to a distance-dependent curve 211. During this transformation it is assumed that the acquired curve 204 has formed exclusively by propagation in a vacuum. By multiplication with the speed of light in the vacuum, the ordinate of the first illustration 201 is converted to a distance axis of the second illustration 202. This distance axis indicates the electrical distance. Furthermore, setting off or taking into account an offset results in the echo 206 caused by coupling-in the high-frequency signal obtaining the distance value of 0 m.

The second illustration 202 shows the echo curve 211 as a function of the electrical distance D. The electrical distance corresponds to the distance which an electromagnetic wave in a vacuum covers in a certain time. The electrical distance essentially does not take into account any influences of a medium, which influences possibly result in slower propagation of the electromagnetic waves. The curve 211 thus represents a non-compensated-for echo curve that is, however, connected to locations.

In the present text electrical distances may be designated by upper-case characters D whereas physical distances that can be measured on the container may be designated by lower-case characters d. The physical distance $d_L$, $d_B$, 113, 114 can be measured on the container.

It may, furthermore, be possible to essentially fully compensate the echo curve 211, i.e. to essentially fully relate the echo curve to a physical distance. The third illustration 203 in FIG. 2 shows such a fully compensated echo curve 212 of the echo curve 211. In order to obtain an illustration of the echoes above the physical distance, in the present case the influence of the overlay medium 107 in the region between locations 0 and $D_L$ of the curve 211 is taken into account. The electrical distance indications of the abscissa between 0 and $D_L$ are converted to physical distance indications according to the following context:

$$d_i = \frac{D_i}{\sqrt{\varepsilon_L \cdot \mu_L}}$$

wherein i denotes a running index relating to distance values between the locations 0 and $D_L$. Since $\varepsilon_{Luft}$ and $\mu_{Luft}$ ($\varepsilon_{Air}$ and $\mu_{Air}$) in good approximation essentially correspond approximately to the value 1, in the present example no correction needs to be made in relation to this section. The electrical distance indications of the abscissa between $D_L$ and $D_B$, which correspond to the region of the container, which region comprises a medium other than air, are, however, converted to physical distance indications according to the following context:

$$d_i = d_L + \frac{(D_i - D_L)}{\sqrt{\varepsilon_M \cdot \mu_M}}$$

wherein i denotes a running index relating to distance values between the locations $D_L$ and $D_B$.

The third illustration 203 of an echo curve shows the corrected gradient or the compensated gradient of the acquired echo curve 204. Both the distance $d_L$ to the echo 209 of the feed material surface 105 and the distance $d_B$ of the echo 210 generated by the lower end 108 of the waveguide 104 essentially correspond to the distances $d_L$, $d_B$, 113, 114 that can be re-measured on the container 100.

Within the context of signal processing 102, 109, 110, 111 in the device 101, in particular in the latter's control apparatus 130, conversion of the acquired curve 204 to curve 211, in other words determination of the electrical distances of various echoes, is carried out essentially in relation to all acquired echoes 205, 206, 207, 208. Conversion of the echo curve 211 to a compensated echo curve 212 is generally-speaking not carried out, because correction of a single fill-level value is sufficient. In other words, in the non-compensated curve 211 only the echo of the feed material surface 105 or the echo generated on the lower end of the waveguide may be compensated.

Figure 3:
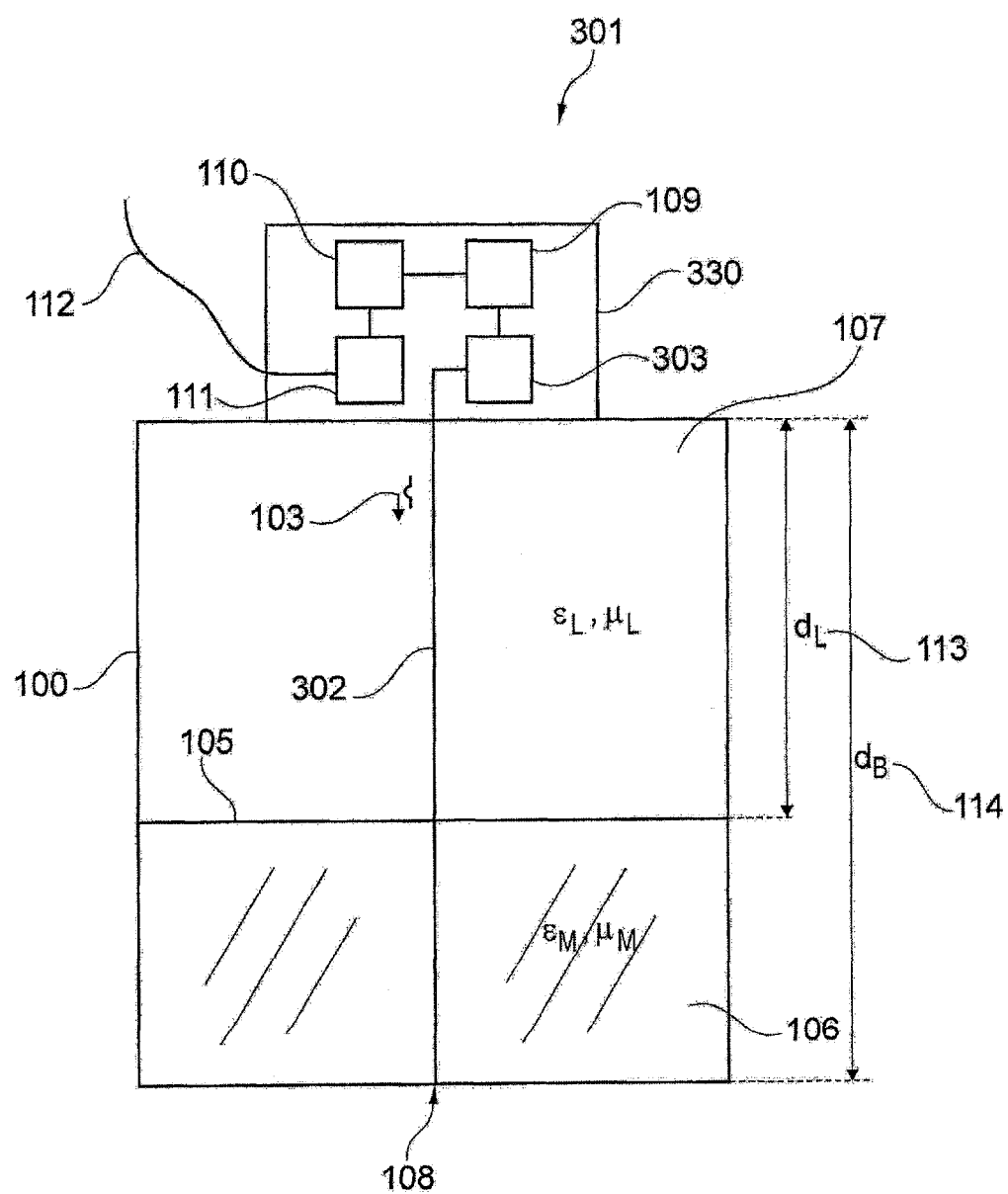
FIG. 3 shows a measuring arrangement with a measuring rod according to the principle of the guided microwave to provide a better understanding of the present invention.

FIG. 3 shows a further arrangement 301 for fill-level measuring according to the principle of the guided microwave. In this arrangement, fill-level measuring takes place by means of a single conductor 302. The device differs by a changed fill-level measuring device 301 that instead of utilizing the coaxial conductor 104 as a probe 302 utilizes a metal bar 302 for guiding a high-frequency signal 103 generated by the high-frequency unit 303 of the control apparatus 330. In other words the fill-level measuring device 301 may comprise a control apparatus 330 and a probe 302. Because of physical law principles, the high-frequency signal 103 can essentially not propagate in the interior of the metal bar 302, but instead moves along the outer surface of the bar, in particular between the bar and the container wall. The echo signals 204, 211, 212 that can be generated with this arrangement, in a rough approximation, essentially correspond to those from FIG. 2, and for this reason the evaluation of the signals and thus the control apparatus 330 essentially do not differ from the control apparatus 130 shown in FIG. 1.

Figure 4:
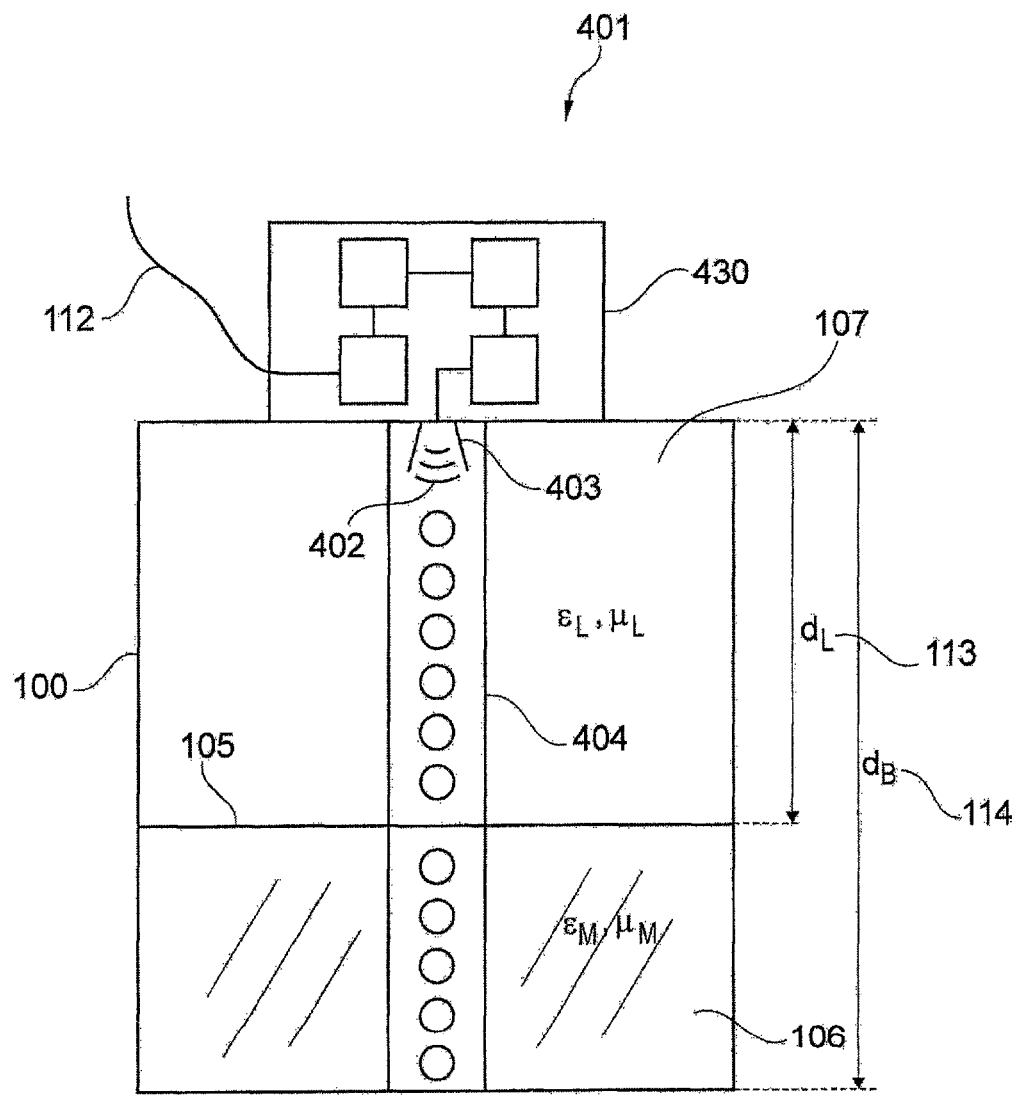
FIG. 4 shows an arrangement with a standpipe for fill-level measuring according to the freely-radiating radar principle to provide a better understanding of the present invention.

FIG. 4 shows a further apparatus 401 for fill-level measuring, which apparatus 401 is designed according to the freely-radiating radar principle. For fill-level measuring according to the freely-radiating radar principle a standpipe 404 can be utilized in order to achieve guidance of the radar rays or generally of an electromagnetic wave. The fill-level measuring device 401, which satisfies the requirements of fill-level measuring according to the freely-radiating radar principle, may comprise the control apparatus 430 for generating and evaluating a radar signal, and may comprise the probe 404 or the standpipe 404. The fill-level measuring device 401 emits the radar signal 402 by way of the feed in device 403 or the antenna 403 into the interior of the standpipe 404, whereupon this radar signal propagates, according to physical law principles, inside the standpipe 404. Operation without a standpipe is also possible, wherein in that case the freely-radiating radar wave is essentially guided by the inner wall of the container. The signals reflected by the feed material 105, in particular by its surface, in turn serve to determine the actual fill level 113 in the container 100. The arrangement according to FIG. 4 can also be utilized for acquiring the fill level by means of acoustic signals or optical signals in the standpipe.

In the arrangement shown in figures FIG. 1, FIG. 3 and FIG. 4 in each case only one measurement or one single measuring principle is used for measuring the fill level with the use of a standpipe. These measurements with the use of only one single measuring principle are a single-channel measurement process. A multi-channel measurement in the context of fill-level measuring technology can, however, offer an effective evaluation of echo curves. In a multi-channel measurement a multi-channel measuring device may be utilized. A multi-channel measuring device may utilize a multi-channel probe, a multi-channel measuring apparatus and/or a multi-channel control apparatus. In combination with a correspondingly adapted control apparatus, instead of or as a supplement to a measured value that indicates the fill level, a further parameter can be stated, for example a material characteristic or a mixing ratio of a medium. The measured value and/or parameter can be provided at a collective interface.

The measuring apparatus, in particular the multi-channel measuring apparatus or multi-channel probe, can be utilized for fill-level measuring and/or separating layer measuring and/or emulsion measuring and/or interface measuring.

Figure 5:
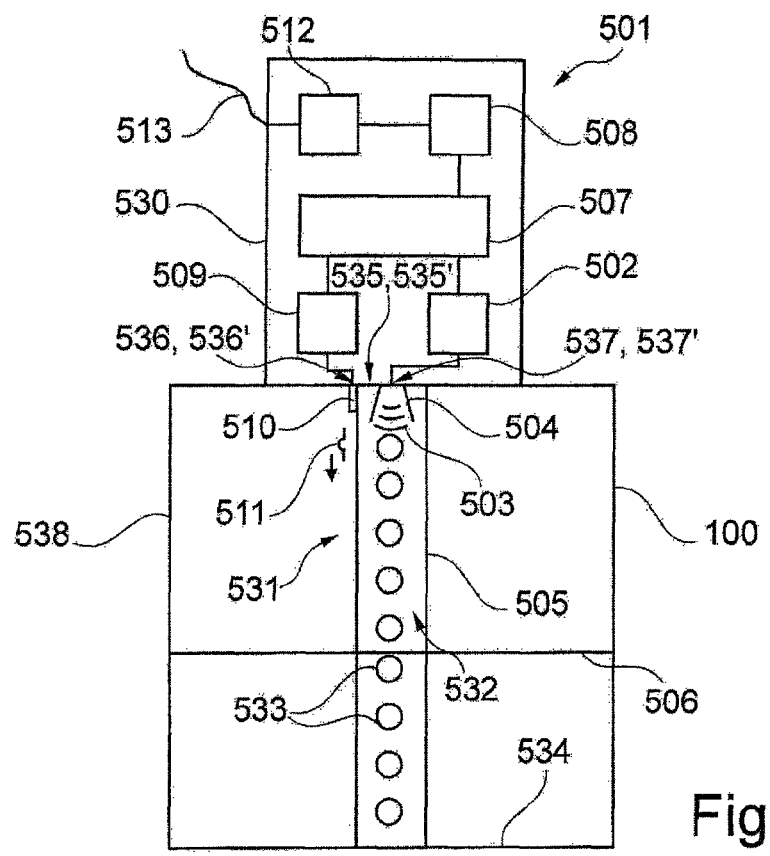
FIG. 5 shows a measuring arrangement for fill-level measuring by means of a freely-radiating electromagnetic wave and a guided microwave according to an exemplary embodiment of the present invention.

FIG. 5 shows an embodiment of a multi-channel measuring device 501 with a multi-channel measuring apparatus 505 and a multi-channel control apparatus 530 according to an exemplary embodiment of the present invention. The multi-channel measuring apparatus 505 comprises a first channel 509, 510, 531 and a second channel 502, 504, 532. By means of a standpipe 505 a multi-channel measurement can thus be carried out.

The fill-level measuring device 501 is designed, by means of a first measuring device 509 or by means of a first high-frequency unit 509, to generate an electromagnetic pulse 511, and to couple the aforesaid, by means of a suitable coupling 510 or a first feed in device 510, into the first waveguide device 531, for example an outside 531 of the standpipe 505. For feeding in or coupling in, the first coupling device 510 or feed in device 510 leads the electromagnetic pulse 511 or the electromagnetic wave 511 to the outside of the standpipe 505. Following feeding in, the electromagnetic pulse 511 propagates along the surface 531 of the standpipe 505 and is reflected by the surface 506 of the medium to be measured. The first high-frequency unit 509 prepares an echo curve from the reflected signals, which echo curve is digitized in the analog-digital converter unit 507 and is forwarded to the evaluation device 508 or evaluation unit 508. The first measuring device 509 and the second measuring device 502 share the analog-digital converter unit 507, i.e. the first measuring apparatus 509 and the second measuring apparatus 502 utilize a shared A/D converter unit 507. By means of this digitized first echo curve, the evaluation unit 508 determines at least one characteristic value relating to the level of the feed material surface 506.

Furthermore, the fill-level measuring device 501 radiates the radar wave 503, which has been generated in the second measuring device 502, in the second channel 502 or in a second high-frequency unit 50, by way of a second feed in device 504 or antenna 504, into the interior of a standpipe 505. The standpipe 505, in particular the inner pipe wall of the standpipe 505, is used as a locally separate measuring device 532 and can be designed as a second waveguide device 532 for the radar wave 503 or for the electromagnetic wave 503. Because of the reflection from the feed material surface 506 the fill-level measuring device 501 is able to form a second echo curve and to digitize it by means of the analog-digital converter unit 507 and to forward it as a digital echo curve 204 to the evaluation device 508 or to the evaluation unit 508. By means of this digitized echo curve the evaluation unit 508 determines at least one further characteristic value relating to the level of the feed material surface 506.

In addition it should be pointed out that this determination of a fill level by means of the measuring device, for example in the interior 532 of a standpipe 505, can be implemented with the use of various measuring principles. Examples of measuring principles on which the measuring device can be based include fill-level measuring processes on the basis of ultrasound or laser, or fill-level measuring processes by means of conductive, inductive or capacitive measuring of the interior space of the standpipe.

The first waveguide device 531 locally separates the measuring device 532 so that the first measuring device 509 acquires the feed material surface 506 at a local position that differs from the position used by the measuring device 532 or gauge device 532. The first waveguide device 531 thus separates two spatial regions 531, 532 from each other. In particular, a probe 505 can provide two spatial regions 531, 532 in which measurements can be carried out.

Furthermore, the evaluation unit 508 is able, with the use of at least one of the characteristic values previously determined from a first measurement and/or a second measurement, relating to the level inside and/or outside the standpipe 505, to determine at least one shared characteristic value relating to the level of the feed material surface 506, which characteristic value following further off-setting by the output device 512 is provided to a shared interface 513. The provision can be implemented in analog form for example as a 4.20 mA signal to a 4.20 mA interface, or in digital form for example to a field bus. A field bus can be a HART®-bus, a Profibus or a Fieldbus Foundation™ field bus.

It is also possible for the evaluation unit 508 to determine expanded information based on the at least two measurements, thus information which essentially does not relate to fill levels. In other words, by means of two-channel measurement or by means of multi-channel measurement it is not only possible to determine a fill level, but also a further result. This can, for example, be ASSET information that provides early identification of prospective malfunctions of the sensors, or information relating to the reliability of the measurement or to the contamination buildup relating to the standpipe.

The standpipe 505 shown in FIG. 5 comprises a multitude of lateral openings 533 in the lateral surface of the standpipe 533, which openings 533 make it possible for a liquid to enter the interior 532 of the standpipe. In an exemplary embodiment the standpipe comprises a single lateral opening or exactly two lateral openings. In one example at least one lateral opening is arranged on the standpipe 505 in such a manner that in an installed state in a container 100 it is located so as to be as close as possible to the container bottom 534 and/or that it is arranged so as to be located as far as possible from the container bottom 534. The term "container bottom" 534 may refer to the region in a container 100 in which region a liquid essentially collects when gravitational force acts on the liquid 506. The openings 533 can be designed as holes, lamellae or slits. The openings can be distributed in an essentially uniform grid along a line or irregularly over the length of the pipe 505. According to another example, except for the openings on the two end faces or face sided of the pipe 505, said pipe 505 essentially comprises no further openings. Generally speaking, a pipe may comprise openings on the end faces. A cover on an end face of the pipe can be utilized as a spacer device. The spacer device can be arranged at any arbitrary position along the length of the pipe.

The measuring apparatus 505 is designed as a multi-channel measuring probe 505. It comprises the spacer device 535 which essentially ensures that the measuring device 532 and the first waveguide device 531 comprise an essentially constant distance over a predeterminable length. The spacer device 535 may thus be designed in such a manner that it can make possible essentially parallel measurement in the two channels 511, 532. In the case in which apart from the first waveguide device 532 the measuring device 531 also utilizes propagation of an electromagnetic wave, the spacer device may essentially ensure that the two waves propagate independently of each other in a parallel direction. Thus, measurement of the fill level 506 may take place at two different locations whose distance from each other is essentially known. The spacer device 535 can be designed so as to match the connection spacer device 535' of the control apparatus 530.

For affixation of the measuring probe 505 to the control apparatus 530 a first connection device 536' and a second connection device 537' can be provided on the control apparatus 530. On the measuring probe a first feed in device 510 with a connection device 536, and a second feed in device 504 with a connection device 537 are provided. The first connection device 536' may be provided for electrical connection to the connection device 536 of the first feed in device 510, for example as a plug/socket combination. The second connection device 537' may be provided for electrical connection to the connection device 537 of the second coupling device 504, for example as a plug/socket combination. For mechanically connecting the measuring apparatus 505 to the control apparatus 530 a matching screw thread and/or a corresponding bayonet socket can be provided. Mechanical coupling can also take place by means of the spacer device 535 or the connection spacer device 535'. The connection spacer device 535' can be used to hold the measuring signal or the electromagnetic wave of the control apparatus 530 at a distance corresponding to the distance between the measuring device and the first waveguide device. In this manner, during mechanical coupling, it is easy to bring about electrical coupling since, by means of the spacer device 535 and the connection spacer device 535', the connection devices 536, 537 of the feed in devices 510, 504 and of the measuring apparatuses 509, 502 are matched to each other. Thus a measuring device 501 for multi-channel measurement can be produced quickly.

Figure 6:
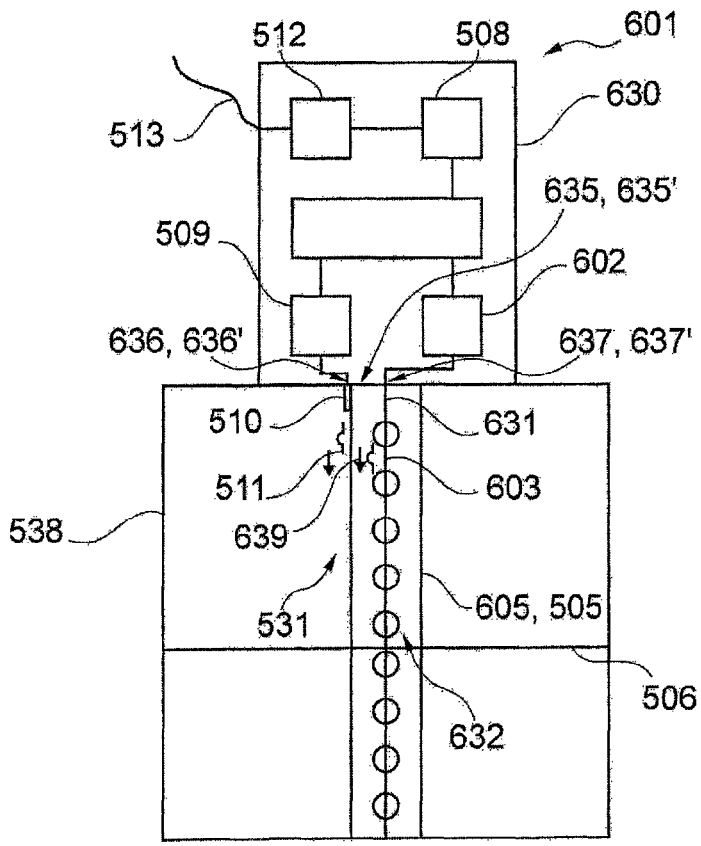
FIG. 6 shows a measuring arrangement for fill-level measuring with two electromagnetic waves according to the principle of the guided microwave according to an exemplary embodiment of the present invention.

FIG. 6 shows a further arrangement 601 for multi-channel fill-level measuring. In the exemplary embodiment of the present invention, according to FIG. 6 a coaxial conductor 605 is utilized as a multi-channel probe. In this variant a standpipe 605, 505 is provided with an inner conductor 603 and forms a coaxial conductor 605 which as a result of being affixed to the control apparatus 630 forms part of the fill-level measuring device 601. The level 506 of the liquid in the interior of this conductor 605 is determined by means of a second electromagnetic pulse 639 that is generated by the second measuring apparatus 602, which is designed as a third high-frequency unit 602. This third high-frequency unit 602 is designed in such a manner that it can excite an electromagnetic wave in the coaxial conductor 605. The first measuring apparatus 509 is designed as a first high-frequency unit 509 and corresponds to the first high-frequency unit 509 of FIG. 5. The first measuring device 509 is utilized for measuring the level 506 of the liquid, corresponding to the method shown in FIG. 5, of measuring the fill level in the first channel 531 along the outer surface of the standpipe 605. Likewise this embodiment of a two-channel measuring 531, 632, shown in FIG. 6, by means of a two-channel measuring probe 605 is used for carrying out two measurements that are independent of each other according to the principle of the guided microwave for fill-level determination, or to carry out double fill-level measuring according to a transit time method.

In the case of a guided microwave the guided wave essentially propagates between a potential and a reference potential. In the case of a bar being used as a waveguide, the bar may carry the potential, and the reference potential may be situated essentially at an infinitely distant point. During propagation of an electromagnetic wave along a surface, such as the surface 531 of a pipe, the potential may be situated on the outside 531 of the pipe or on the lateral surface of the pipe, and the reference potential may be situated on the inner side of a container wall 538. Thus, a medium can be measured which is located between the container wall 538 and the lateral surface 531 of the pipe 505, 506. In the case of a coaxial conductor 605 the potential may be situated on the inner conductor 603, and the reference potential may be situated on an outer conductor, for example of the lateral surface of a pipe 605, in particular of the inner surface of a pipe wall.

The feed in devices 510, 504, 631 may be designed for feeding in a signal 511, 503, 603 which they receive by way of the connection devices 536, 537, 636, 637 of the feed in devices or by way of the connection devices 536', 537', 636', 637' of the measuring apparatuses 509, 502, 602 into the corresponding channels 531, 532, 632. In particular, the coupling device 510, 504, 631 may ensure that the waves 511, 639 can propagate in the desired regions, spatial regions 531, 532, 632 or channels. Thus, a first electromagnetic wave 511 may propagate in a first channel 531, and a second electromagnetic wave 639 may propagate in a second channel 632. The feed in device 510, 504, 631 may care for the assignment of the potential and of the reference potential for the purpose of propagation. For said assignment the feed in device can comprise a potential separation device. In order to allow propagation the feed in device may assign the potential.

The feed in devices 510, 631 comprise the connection devices 636, 637 which ensure electrical coupling of the probe 605 to the control apparatus 630 to corresponding connection devices 636', 637'. The spacer device 635 and the connection spacer device 635', respectively, apart from ensuring local separation of the feed in devices 510, 631 and of the connection devices 636, 637, respectively, can also ensure assignment of the potentials.

The two channels 531, 632 form in the interior and in the exterior of the coaxial conductor 605, in other words essentially between the standpipe 605 and the container wall 538 or between the inner conductor 631 and the outer conductor 605.

Figure 7:
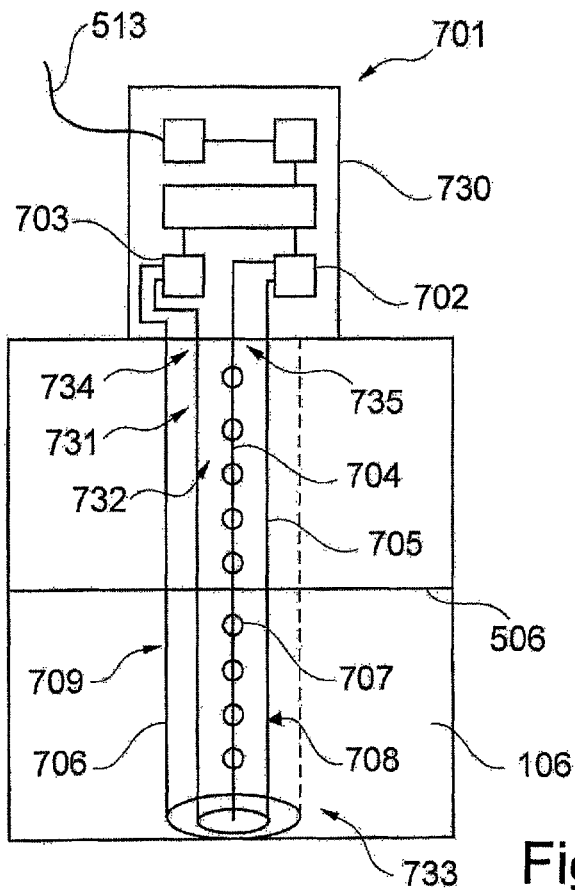
FIG. 7 shows a further measuring arrangement for measuring a fill level with two electromagnetic waves according to the principle of the guided microwave according to an exemplary embodiment of the present invention.

FIG. 7 shows a further probe 733 according to an exemplary embodiment of the present invention. The fill-level measuring device 701 again comprises two measuring apparatuses 702, 703 or high-frequency units 702, 703, which are independent of each other and are utilized for measuring the fill level according to the principle of the guided microwave on two different paths 731, 732 or in two different channels 731, 732 or for measuring said fill level in a locally separated manner or for measuring the fill level with two different methods. Local separation takes place along a radial direction of the coaxially arranged waveguides, i.e. essentially so as to be perpendicular to a direction of propagation of the guided wave. The two channels are formed by a double coaxial conductor in which a coaxial conductor 708 comprising the standpipe 705 as an outer conductor 705 and the bar 704 as an inner conductor 704 is enclosed by a hollow conductor 706 so that the coaxial conductor and the hollow conductor are arranged so as to be essentially coaxial to each other in relation to a longitudinal axis. The probe 733 thus essentially comprises two coaxially arranged pipes 705, 706.

The first measurement 731 uses the outer coaxial conductor 709 for determining a fill-level value or for determining the fill level, wherein the outer coaxial conductor 709 comprises the casing pipe 706, the coating pipe 706 or standpipe 706 as an outer conductor and the pipe 705 as an inner conductor. The second measurement 732 uses the inner coaxial conductor 708 for determining the fill-level value. The pipe 706 of the outer coaxial conductor 709 forms the shared housing of the probe 733. Thus the first channel 731 and the second channel 732 share the middle conductor 705 or center conductor 705 as an outer conductor 705 and an inner conductor 705, respectively. A decision as to whether the middle conductor 705 is used as an inner conductor 705 for the outer conductor 706 or as an outer conductor 705 for the inner conductor 704 depends on the wiring of the feed in device 734 of the outer conductor and on the wiring or connection of the feed in device 735 of the inner conductor. The middle guide 705 can be of a multi-layer design. For example, the middle conductor can comprise a conductive outer conductor and a conductive inner conductor, which conductors are essentially insulated from each other by means of a dielectric material so that both local separation and electrical separation is achieved. The outer conductor or the outside of the middle conductor 705 can be the inner conductor of the first channel 731, and the inner conductor or the inside of the middle guide 705 can also be the outer conductor of the second channel 732. Depending on the application of the probe, the inner coaxial conductor 708 and the outer coaxial conductor 709 can comprise regular holes 707 or openings 707 that make it possible for the liquid 106 to be measured to enter. To illustrate the inner coaxial conductor 708, which would otherwise be hidden by the outer coaxial conductor 709, part of the pipe wall of the casing pipe 706 is shown in a dashed line in FIG. 7. Moreover, FIG. 7 shows the open lower end faces or face sides of the pipes 705 and 708 opposite the feed in devices 734, 735. The two regions, which the probe 733 separates, correspond to the two channels 731, 732, in each case between the inner conductor 704, 705 or the outer conductor 706, 705.

Figure 8:
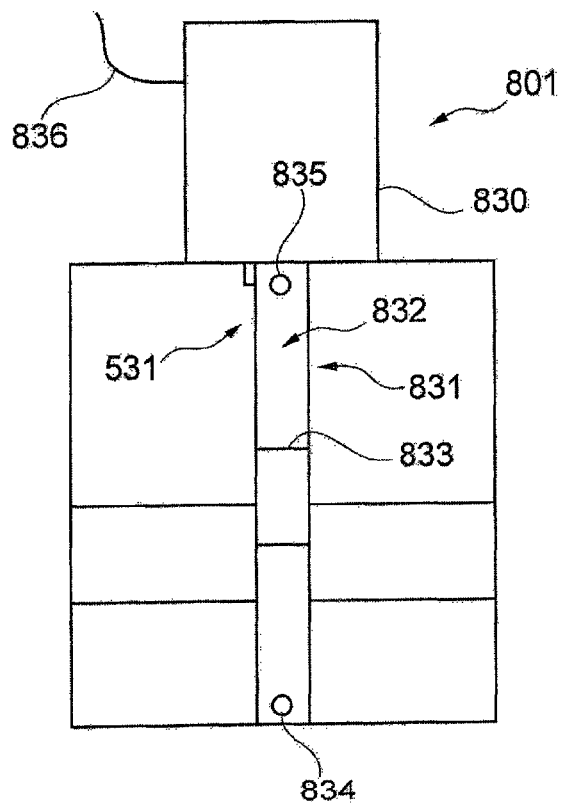
FIG. 8 shows a measuring arrangement for measuring an emulsion according to an exemplary embodiment of the present invention.

FIG. 8 shows a measuring device 801 for measuring separating layers and/or emulsions by means of a standpipe. The measuring device 801 comprises the control apparatus 830 and the probe 831. The probe 831 is designed in such a manner that the liquid level in a second channel 832 differs from that in a first channel 531. The constructional embodiment of the probe 831 with essentially only two lateral openings 834, 835 may prevent, for example, a separating layer of a liquid 833, which separating layer has formed in the interior 832 of the probe, from mixing as a result of a mixer or stirrer. A probe 831 designed in this manner may make it possible for the probe 831 to be utilized for emulsion measuring in a standpipe. To this effect, characteristic values can be determined from the at least two measurements in the two channels 531, 832, which characteristic values are required in the context of separating layer measuring and/or emulsion measuring. In other words, a probe for emulsion measuring may be designed in such a manner that within a container it can separate two regions 531, 831 or channels 531, 831, wherein in one region a mixed emulsion comprising several liquids can be measured, and in the other region a separating layer between the liquids, which separating layer has arisen as a result of de-mixing, can be measured. By way of the collective interface 836 an associated control apparatus 830 can output a characteristic value relating to the emulsion.

Figure 9:
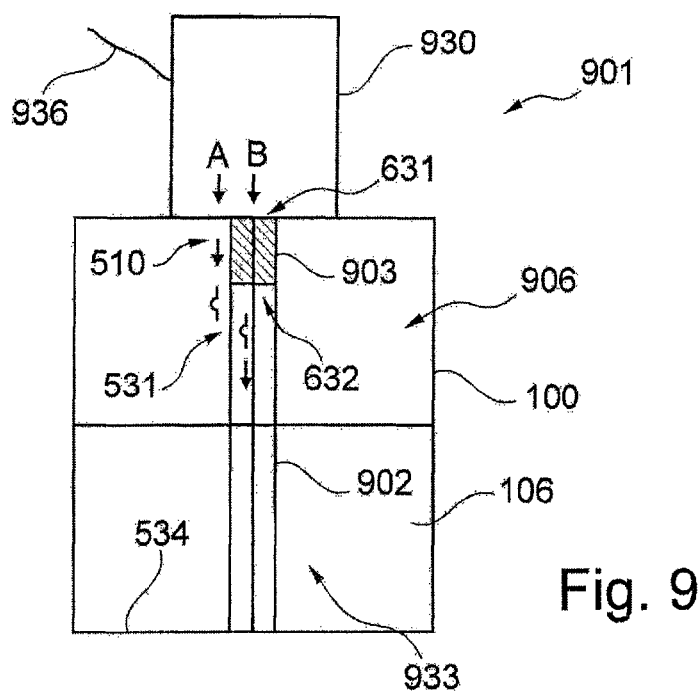
FIG. 9 shows a measuring arrangement for determining media characteristics during fill-level measuring according to an exemplary embodiment of the present invention.

FIG. 9 shows a measuring device 901 for measuring or determining the media characteristics of an overlay atmosphere. The measuring device comprises the probe 933 and the control apparatus 930. The probe 933 or measuring apparatus 933 is a waveguide 902 whose interior has at least partly been filled with a dielectric material 903. The dielectric material 903 is arranged in an upper region of the hollow conductor 902, of the waveguide 902, of the coaxial conductor 902 or of the standpipe 902. In this arrangement the upper region is essentially opposite a container bottom 534 near the second feed in device 631 of a second channel 632, B. By means of a first channel 531, A the outside of the waveguide 902 can be measured. Because of the different measurements in the two channels A, B a media characteristic of the overlay atmosphere 906 or of the overlay liquid 906 can be determined. The dielectric material 903 delays the propagation of the wave in the interior of the probe 933, which wave is used for measuring. In this manner it is possible for the two signals in the two channels 631, 632 to comprise different transit times although the physical distance which they travel to reach the feed material 106 is essentially the same or essentially identical. By means of the different echo curves which in this process arise in the two channels A, B, in particular the dielectric constant and/or the permittivity value of an overlay atmosphere 906 or overlay liquid 906 that forms above the feed material 106 or above the liquid 106 can be determined. By way of the collective interface 936 an associated control apparatus 930 can output a characteristic value relating to the overlay atmosphere 906 or overlay liquid 906.

Since a characteristic value can be output by way of the shared collective interface 513, 836, 936, a measuring device 501, 601, 701, 801, 901 only occupies a single connection on an evaluation device. Taking together at least two channels or several channels in a single probe 733, 505, 605, 831, 902, in particular taking together several channels in a shared housing, for example by means of the spacer device 535, 535', 635, 635', can make it possible for the probe to occupy only one single process opening of a container 100. Thus a space-saving and compact arrangement of two measuring channels is possible.

FIG. 10A shows a simple block diagram of a control apparatus 1010 or of a device 1010 for fill-level measuring. For adaptation to the plurality of channels A, B, 531, 532, 632, 731, 732 or to the at least two channels provided by the measuring apparatus 505, 605, 933, 733, a corresponding design of the device electronics can be implemented that makes it possible to operate at least two channels of a probe. The connection devices on the feed in devices 504, 510, 734, 735 of the probe or the probe connections may generally be designated with the letters A and B in order to illustrate that these are two channels, without, however, going into the type of connection or the type of the coupling device. The channels A, B may be spaced apart by means of the connection spacer device by a distance that may correspond to a distance of the associated connections of the feed in devices.

FIG. 10A shows that it is possible, by means of the evaluation device 1011, to combine two complete electronics inserts 1012, 1013 or electronic modules 1012, 1013 of two individual associated control apparatuses of two arbitrary fill-level measuring devices in order to arrive at a shared characteristic value on the collective interface 1014. In this arrangement the evaluation device is used for the evaluation of two measuring results of two different measuring devices 101, 301, 401 that operate according to the single-channel principle. The individual measuring devices, in particular the associated control apparatus that operate according to the single-channel principle, can also be utilized for operating the individual channels of a multi-channel probe. The measuring device or an associated probe that operates according to the single-channel principle essentially only supports carrying out a single measurement, because it may be the case, for example, that no further feed in device has been provided for an additional measurement. The electronics inserts may thus operate according to various principles, suitable for the embodiment of the probe feed ins or the probe couplings that are used at the connections A and B. The overall evaluation unit 1011 offsets the individual characteristic values provided by the electronics inserts 1012, 1013, which characteristic values can, for example, be determined from measurements A and B that have been carried out in parallel or in series, and from them forms at least one shared measured value that is provided on the shared external interface 1014. This shared measured value may be a characteristic value that essentially can be determined only by carrying out at least two measurements, in particular a characteristic value that essentially can be determined only by carrying out at least two measurements at different locations. In other words, the characteristic value may essentially be determined only by carrying out two individual measurements for fill-level measuring and/or limit-level measuring.

FIG. 10B shows a block diagram of a control apparatus 1020 in which the measured-value processing of the two channels, in particular the first measuring apparatus 1012b and the second measuring apparatus 1013b, and the evaluation device 1027 are integrated in a shared housing. The measuring apparatuses 1012b, 1013b can be individual fill-level measuring devices, in particular their control apparatuses or evaluation electronics. The functionality of a control apparatus 1020 according to FIG. 10B essentially corresponds to the functionality of the control apparatus 1010 according to FIG. 10A, wherein the design or the electronics of the measuring device 1012, 1013 is/are shown in greater detail. The first measuring device 1012b comprises the high-frequency generating unit 1021, the analog-digital converter unit 1023 and the evaluation unit 1025, which units are adapted for cooperating in such a manner that in combination they can carry out a first measurement in the first measuring channel A and can form a first measured value, e.g. a fill-level measuring value. Furthermore, the second measuring device 1013b comprises the high-frequency generating unit 1022, the analog-digital converter unit 1024 and the evaluation unit 1026, which units are adapted for cooperating in such a manner that in combination they can carry out a second measurement in the second measuring channel B and can form a second measured value, e.g. a fill-level measuring value. For carrying out the measurements, the control apparatus can provide on the first connection device 1001 an electromagnetic wave and on the second connection apparatus 1002 a measuring signal, for example a second electromagnetic wave. The control apparatus 1020 may comprise at least three external interfaces. In one example the control apparatus 1020 can comprise only 3 external interfaces. Two of the external interfaces 1001, 1002 may be used for providing a measuring signal, and/or for receiving an echo signal, and the third may be used as a collective interface 1014 for providing a shared measured value. The measured values in the two channels A, B are offset against each other by a suitable program logic in the output unit 1027 and are provided towards the outside via the collective interface 1014. The output unit 1027, the first evaluation unit 1025 and the second evaluation unit 1026 may form a shared evaluation unit or a shared evaluation device. Measuring with the second measuring apparatus B can also be implemented according to an alternative measuring principle that differs from a guided or freely-propagating electromagnetic wave. The high-frequency unit 1022 then comprises a suitable unit for generating the measuring signal, for example a laser generating unit, an optical signal source, an ultrasound generating unit, an acoustic signal source, a signal source for carrying out a capacitive measurement, and/or a signal source for carrying out an inductive measurement. Likewise, the measuring signal is provided via a connection device 1002 that corresponds to the measuring signal.

FIG. 10C shows a further implementation variant of a control apparatus 1030. In the control apparatus 1030 the first measuring device 1012c and the second measuring device 1013c with the output unit 1037 are accommodated in a shared housing. For evaluation of the digitized echo curves or measured values of the channels A and B, which are provided on the connections 1031 and 1032, the control apparatus 1030 utilizes a shared evaluation unit 1033. Consequently, the evaluation unit 1033 comprises precisely three connections. By means of one connection the evaluation unit 1033 is connected to the output unit 1037; by means of the second connection the evaluation unit 1033 is connected to the first channel A 1012c; and by means of the third connection the evaluation unit 1033 is connected to the second channel B 1013c. In other words, the first measuring device 1012c and the second measuring device 1013c share a common evaluation unit 1033 or evaluation device 1033.

As shown in the block diagram of FIG. 10D it can also be provided for the first measuring device 1012d and the second measuring device 1013d to share an A/D converter. Converting the signals of the two channels A, B to a digital presentation can be carried out with a single analog-digital converter unit 1041 inside the control apparatus 1040. For utilizing a shared analog-digital converter unit 1041 the control apparatus 1040 comprises an analog switch 1042 which forwards the analog and low-frequency signals of the channels A, B in a time multiplex method to the analog-digital converter unit 1041. The time multiplex method can be a time-division multiplex method. Because of the shared utilization of the A/D converter unit 1041 the measurements in the two channels A, B take place in a chronologically sequential manner. For this reason the evaluation unit 1043 essentially comprises only two connections. By way of one connection the evaluation unit 1043 receives the time multiplex signal from the A/D converter 1041. By way of the other connection said evaluation unit 1043 conveys a processed signal, which it has obtained from the measuring signals of the channels A, B, to the output unit 1037.

The block diagram of a control apparatus 1050 of a sensor or measuring device according to FIG. 10E shows a circuit arrangement in which the two measuring apparatuses 1012e, 1013e share an existing high-frequency unit 1051. In order to utilize this shared arrangement of the high-frequency unit 1051 a high-frequency change-over device 1052 is provided. By means of this circuit arrangement many components of the control apparatus can be utilized in a shared manner by both channels A, B or by both measuring apparatuses 1012e, 1013e, and consequently a simple design of the control apparatus 1050 becomes possible. By means of a targeted utilization of shared-use facilities it is possible to reduce the manufacturing costs of a fill-level measuring device.

In the figures FIG. 10A to FIG. 10E the shared housing of the control apparatus can comprise the connection spacer device 1003 which holds the connection devices 1001, 1002 and in particular the channels A, B at a particular distance from each other. This distance may be suitable for a probe that is to be operated by means of the respective control apparatus. By providing different distances it is possible to implement housing coding by means of which it can be provided for only the matching probes to be used with a control apparatus. The switching arrangements of figures FIG. 10A to 10E can be implemented as an integrated circuit.

A 50 Ohm coaxial cable can be provided as a connection device 1001, 1002 of the control apparatus or as a connection device of the feed in device.

Figure 11:
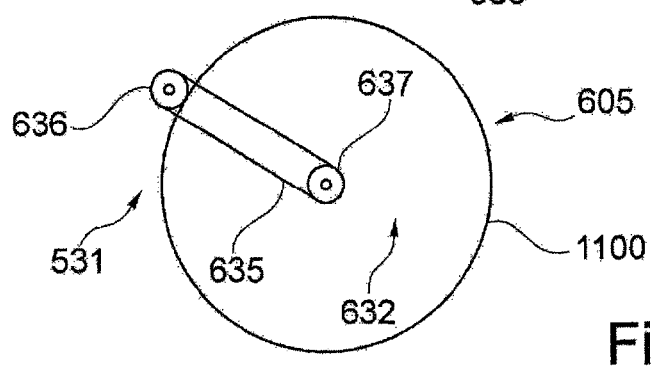
FIG. 11 shows a top view of the measuring apparatus or measuring arrangement of FIG. 6 according to an exemplary embodiment of the present invention.

FIG. 11 shows a top view of a measuring apparatus 605 or measuring arrangement of FIG. 6 which operates according to the two-channel principle. The measuring apparatus comprises the standpipe 605 on which two measuring channels 531, 632 are formed by means of the spacer device 635 and/or the partition wall 1100. The measuring channels 531, 632 are situated inside and outside the standpipe 605. A measuring signal, for example an electromagnetic wave, can be impressed on these measuring channels 531, 632 by way of the connection devices 636, 637 of the feed in devices, which are not shown in FIG. 12. Propagation of the measuring signals in the channels 531, 632 takes place independently of each other so that independently of each other a fill level can be measured at defined positions. From the locally different measuring results, apart from the fill level, further parameters can be derived. The position of the measurements is essentially determined by the arrangement of the spacer device 635. The connection devices 636, 637 of FIG. 12 are designed as coaxial sockets.

Figure 12:
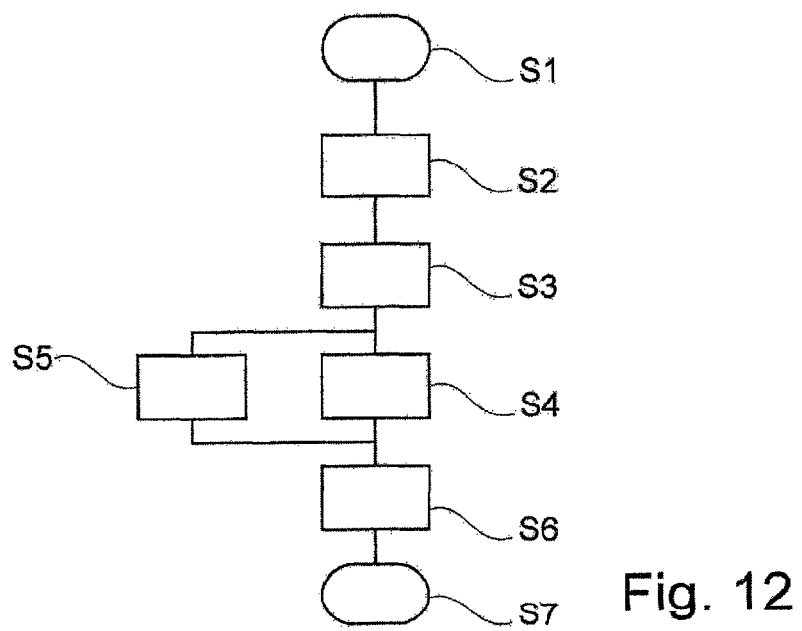
FIG. 12 shows a flow chart relating to a method for operating a measuring apparatus according to an exemplary embodiment of the present invention.

FIG. 12 shows a flow chart relating to a method for operating a measuring apparatus, which operates according to the two-channel principle, according to an exemplary embodiment of the present invention. Starting from an idle state S1, in step S2 provision of a first electromagnetic wave in a first waveguide device 1100 by way of a first connection device 636 takes place.

Step S3 provides for measuring at least part of the first waveguide device 1100 with a measuring device 632 or a second waveguide device 632 that comprises a second connection device 637', wherein the first connection device 636' is spaced apart from the second connection device 637' by means of the connection spacer device 635'. The connection spacer device 635' can be designed in the same manner as the spacer device 635 of the probe. The spacer device can also be formed by a shared housing in which the control apparatus is accommodated.

In a further step S4 a first measured value of a measurement with the first electromagnetic wave is provided on an evaluation device. This measured value is obtained from evaluating the echo curve of the first electromagnetic wave.

Essentially concurrently with step S4 or parallel to step S4, in the step S5 the provision of a second measured value of a measurement by means of the measuring device 632 to the evaluation device takes place. In a further exemplary embodiment the provision of the first measured value takes place prior to the provision of the second measured value. In yet another exemplary embodiment the provision of the first measured value takes place chronologically after the provision of the second measured value. In a corresponding sequence the provision of the first electromagnetic wave and of the measuring signal of the measuring device 632 can take place in step S2 or S3.

In step S6 the measuring results are taken together and/or are evaluated. For example, the first measured value and the second measured value are converted to a shared measured value and the shared measured value is provided at a collective interface of the evaluation device. By way of the collective interface it is also possible to provide a parameter of the feed material or of a container content, which parameter differs from a fill level and indicates, for example, a media characteristic or a mixing ratio.

In a further exemplary embodiment of the present invention, according to a first aspect a apparatus 501, 601, 701, 801, 901 for measuring a fill level, a separating layer or an emulsion according to a transit time method is stated, wherein the apparatus comprises a media-contacting standpipe 505, 605, 733 and a first evaluation unit 1025. The first evaluation unit 1025 is designed in such a manner that it can determine at least one characteristic value relating to a first fill level, to a first separating layer and/or to a first emulsion inside the media-contacting standpipe 505, 605, 733, 831, 933.

The apparatus 501, 601, 701, 801, 901 further comprises a further evaluation unit, wherein the further evaluation unit 1026 is designed in such a manner that it determines at least one characteristic value relating to a further fill level, to a further separating layer and/or to a further emulsion, which is determined outside the media-contacting standpipe 505, 605, 733, 831, 933. In an example the characteristic value is determined outside the media-contacting standpipe. For determining the at least one characteristic value relating to a further fill level, to a further separating layer and/or to a further emulsion a microwave is guided along the outer surface of the media-contacting standpipe.

In a second aspect of the present invention the apparatus according to the first aspect is stated, wherein the first evaluation unit 1025 and the further evaluation unit 1026 are essentially identical 1033 either partially or entirely.

In a third aspect of the present invention the apparatus according to the first aspect or according to the second aspect is stated, wherein the distance of the first fill level and the distance of the further fill level from the control apparatus is identical. The distance of the first fill level and of the further fill level from the control apparatus may be measured along a direction of propagation of the electromagnetic wave during emitting.

In a fourth aspect of the present invention the apparatus according to any one of the first to the third aspects is described, which apparatus further comprises a unit 1011, 1027, 1033 for determining at least one characteristic value relating to the fill level and/or to the position of a separating layer, and/or to the composition of an emulsion, wherein to this effect the at least one first value and the at least one further value are used.

In a fifth aspect of the present invention the apparatus according to the fourth aspect is described, wherein the first evaluation unit, the further evaluation unit and/or the unit for determining at least one characteristic value relating to the fill level are identical either partially or entirely.

In a sixth aspect of the present invention the apparatus according to any one of aspects one to five is stated, which device further comprises an inner guide 603, 704 that is guided inside the media-contacting standpipe 605, 708, wherein the inner guide and the media-contacting standpipe form a coaxial guide.

In a seventh aspect of the present invention the apparatus according to the sixth aspect is stated, wherein the first evaluation unit 1025 is designed for determining the at least one characteristic value relating to a first fill level in the media-contacting standpipe according to the principle of the guided microwave.

In an eighth aspect of the present invention the apparatus according to any one of aspects one to seven is stated, which device furthermore comprises at least one casing pipe 706 that encloses the standpipe, wherein this at least one casing pipe 706 forms the outer guide of at least one further coaxial line 708, wherein the further evaluation unit is designed for determining the at least one characteristic value relating to a fill level, to the separating layer or to the emulsion with the use of the at least one further coaxial line.

The first measuring device 703 can comprise two connections, wherein one connection is connected to the outer pipe 706, and the other connection is connected to the inner pipe 705. The second measuring device 702 can comprise two connections, wherein one connection is connected to the inner pipe 705, and the other connection is connected to the bar 704. One connection may be a connecting cable.

In addition, it should be pointed out that "comprising" does not exclude other elements or steps, and "a" or "one" does not exclude a plural number. Furthermore, it should be pointed out that characteristics or steps which have been described with reference to one of the above exemplary embodiments can also be used in combination with other characteristics or

The invention claimed is:

1. A measuring apparatus, comprising:
   a first waveguide device with a first feed in device, the first waveguide device carrying out a first measurement;
   a measuring device carrying out a second measurement; and
   a spacer device
   wherein the first waveguide device is adapted for dividing a container interior into at least one first spatial region and into a second spatial region;
   wherein the first waveguide device is adapted for guiding a first electromagnetic wave in the first spatial region, which first electromagnetic wave has been coupled into the first waveguide device via the first feed in device;
   wherein the measuring device is adapted for carrying out the second measurement on the first waveguide device in the second spatial region;
   wherein the first waveguide device is adapted for spacing apart the first feed in device of the first waveguide device from the measuring device so that the first electromagnetic wave propagates in the first spatial region between a first potential and a first reference potential at a predeterminable distance from the second spatial region provided for carrying out the second measurement by the measuring device;
   wherein the first spatial region differs from the second spatial region;
   wherein the measuring device is adapted as a second waveguide device with a second feed in device, wherein the second waveguide device is adapted for guiding a second electromagnetic wave in the second spatial region between a second potential and a second reference potential, which second electromagnetic wave has been coupled into the second waveguide device via the second feed in device; and
   wherein the spacer device is configured for spacing apart the first feed in device and the second feed in device and for the assignment of the first and second potentials and the first and second reference potentials.

2. The measuring apparatus according to claim 1, wherein the spacer device is further adapted for spacing apart the first feed in device of the first waveguide device from the measuring device so that the first electromagnetic wave propagates in the first spatial region at a predeterminable distance from the second spatial region provided for carrying out the second measurement by the measuring device.

3. The measuring apparatus according to claim 2, wherein the spacer device is at least one spacer device selected from the group of spacer devices consisting of:
   a bracket;
   a holder for a metal bar;
   a holder for a cord;
   a flange;
   a container wall;
   a wall of a waveguide; and
   an isolator.

4. The measuring apparatus according to claim 1, wherein at least one of the first waveguide device and the second waveguide device includes at least one waveguide device selected from the group of waveguide devices consisting of:
   an optical waveguide;
   a coaxial conductor;
   a hollow conductor;
   a hollow conductor comprising at least one opening;
   a guiding device for a microwave;
   a standpipe;
   a wire;
   a metal bar; and
   a cord.

5. The measuring apparatus according to claim 1, wherein the first waveguide device and the second waveguide device are arranged coaxially.

6. The measuring apparatus according to claim 1, wherein at least one of the first waveguide device and/or the second waveguide device includes an end;
   wherein through this end a reference line extends so as to be perpendicular to a direction of propagation of the electromagnetic wave; and/or
   wherein the first feed in device and the second feed in device are arranged in the equal space relative to this reference line.

7. The measuring apparatus according to claim 1, wherein at least one of the first feed in device and the second feed in device includes at least one feed in device selected from the group of feed in devices consisting of:
   a strip conductor;
   an inductive coupler;
   a capacitive coupler;
   a loop coupling;
   a pin coupling; and
   a hole coupling.

8. The measuring apparatus according to claim 1, wherein the first feed in device and the second feed in device include a connection device, and wherein the connection device is at least one connection device selected from the group of connection devices consisting of:
   a high-frequency plug;
   a 50 Ohm coaxial plug;
   a high-frequency socket;
   a 50 Ohm coaxial socket;
   a high-frequency adapter;
   a circulator; and
   a directional coupler.

9. The measuring apparatus according to claim 1, wherein the measuring apparatus is adapted as a probe for a fill-level measuring device and/or for a limit-level measuring device.

10. A control apparatus, comprising:
    an evaluation device;
    a first measuring device with a first connection device;
    a second measuring device with a second connection device;
    a connection spacer device;
    a collective interface;
    wherein the first measuring device and the second measuring device are connected to the evaluation device;
    wherein the first measuring device is adapted for providing a first electromagnetic wave via the first connection device for a first spatial region of a first waveguide device;
    wherein the second measuring device is adapted for providing a measuring signal for measuring at least part of the first waveguide device in a second spatial region via the second connection device;
    wherein the first connection device is spaced apart from the second connection device by the connection spacer device so that the first electromagnetic wave is provided at a distance from the measuring signal, which distance is predeterminable by the connection spacer device;

wherein the first measuring apparatus is adapted for providing a first measured value of a first measurement with the first electromagnetic wave to the evaluation device;

wherein the second measuring apparatus is adapted for providing a second measured value of a second measurement with the measuring signal to the evaluation device;

wherein the evaluation device is adapted for converting the first measured value and the second measured value to a shared measured value and for providing the shared measured value to the collective interface.

wherein the measuring signal is a second electromagnetic wave; and wherein the control apparatus further comprising:

a shared generator generating the first electromagnetic wave and the second electromagnetic wave; and a distribution device adapted for distributing the first electromagnetic wave to the first connection device, and the second electromagnetic wave to the second connection device.

11. A method for operating a measuring apparatus, comprising:

generating a first electromagnetic wave and a second electromagnetic wave in a shared generator;

providing the first electromagnetic wave in a first spatial region of a first waveguide device via a first connection device;

measuring at least part of the first waveguide device with a measuring device in a second spatial region that comprises a second connection device, wherein the first connection device is spaced apart from the second connection device by a connection spacer device;

providing a first measured value of a first measurement with the first electromagnetic wave to an evaluation device;

providing the second electromagnetic wave with the measuring device to the second connection device;

providing the second measured value of a second measurement with the second electromagnetic wave to the evaluation device; and converting the first measured value and the second measured value to a shared measured value and providing the shared measured value to a collective interface of the evaluation device.

12. A non-transitory computer-readable storage medium, wherein the computer-readable storage medium comprises a program code which when executed by a processor instructs the processor to carry out the following steps:

generating a first electromagnetic wave and a second electromagnetic wave in a shared generator;

providing the first electromagnetic wave in a first spatial region of a first waveguide device via a first connection device;

measuring at least part of the first waveguide device with a measuring device in a second spatial region that comprises a second connection device, wherein the first connection device is spaced apart from the second connection device by a connection spacer device;

providing a first measured value of a first measurement with the first electromagnetic wave to an evaluation device;

providing a second measured value of a second measurement with the measuring device to the evaluation device;

providing the second electromagnetic wave with the measuring device to the second connection device;

providing a second measured value of the second measurement with the second electromagnetic wave to the evaluation device; and converting the first measured value and the second measured value to a shared measured value and providing the shared measured value to a collective interface of the evaluation device.

* * * * *